(12) United States Patent
Srinivasan et al.

(10) Patent No.: US 7,517,696 B2
(45) Date of Patent: Apr. 14, 2009

(54) CHEMICAL SUPPRESSORS AND METHOD OF USE

(75) Inventors: Kannan Srinivasan, Sunnyvale, CA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 1047 days.

(21) Appl. No.: 10/356,345

(22) Filed: Jan. 30, 2003

(65) Prior Publication Data

US 2004/0149581 A1 Aug. 5, 2004

(51) Int. Cl.
*G01N 30/84* (2006.01)
(52) U.S. Cl. .................. 436/174; 436/149; 436/161
(58) Field of Classification Search ............... 422/70, 422/99; 436/161, 149–151, 174, 176–178; 210/656, 198.2; 73/61.55, 61.58
See application file for complete search history.

(56) References Cited

U.S. PATENT DOCUMENTS

| 3,897,213 A | 7/1975 | Stevens et al. |
| 3,920,397 A | 11/1975 | Small et al. |
| 3,925,019 A | 12/1975 | Hamish et al. |
| 3,926,559 A | 12/1975 | Stevens |
| 4,265,634 A | 5/1981 | Pohl |
| 4,403,039 A | 9/1983 | Ban et al. |
| 4,459,357 A | 7/1984 | Jansen et al. |
| 4,474,664 A | 10/1984 | Stevens et al. |
| 4,751,004 A | 6/1988 | Stevens et al. |
| 4,999,098 A | 3/1991 | Pohl et al. |
| 5,045,204 A | 9/1991 | Dasgupta |
| 5,248,426 A | 9/1993 | Stillian et al. |
| 5,352,360 A | 10/1994 | Stillian et al. |
| 5,597,481 A | 1/1997 | Stillian et al. |
| 6,077,434 A | 6/2000 | Srinivasan et al. |
| 6,436,719 B1 | 8/2002 | Srinivasan et al. |
| 2003/0173222 A1* | 9/2003 | Srinivasan et al. .......... 204/524 |

FOREIGN PATENT DOCUMENTS

WO        WO 0221121        3/2002

* cited by examiner

*Primary Examiner*—Jan M Ludlow
(74) *Attorney, Agent, or Firm*—Morgan, Lewis & Bockius LLP; David J. Brezner

(57) ABSTRACT

A non-electrolytic method and apparatus for treating an aqueous sample stream including analyte ions and matrix ions of opposite charge, for pretreatment or suppression. The apparatus includes an ion exchange membrane capable of passing only ions of opposite charge to the analyte ions, a sample stream flow channel, a first aqueous stream ion receiving flow channel adjacent one side of the sample stream flow channel and separated therefrom by the first ion exchange membrane, and stationary flow-through ion exchange packing disposed in the sample stream flow channel. The ion receiving channel has an ion exchange capacity for the matrix ions less than about 25% of the ion exchange capacity for the matrix ions.

3 Claims, 1 Drawing Sheet

CHEMICAL SUPPRESSORS AND METHOD OF USE

BACKGROUND OF THE INVENTION

The present application relates to a chemical suppression device and method for reducing the concentration of matrix ions of opposite charge to ions to be analyzed, and specifically for use of an ion chromatography suppressor or to a pretreatment device.

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed but not that of the separated ions so that the latter may be determined by a conductivity cell. This technique is described in detail in U.S. Pat. Nos. 3,897,213; 3,920,397; 3,925,019; and 3,926,559.

Suppression or stripping of the electrolyte is described in the above prior art references by an ion exchange resin bed. A different form of suppressor column is described and published in U.S. Pat. No. 4,474,664, in which a charged ion exchange membrane in the form of a fiber or sheet is used in place of the resin bed.

The sample and eluent are passed on one side of the membrane with a flowing regenerant on the other side, the membrane partitioning the regenerant from the effluent of chromatographic separation. The membrane passes ions of the same charge as the exchangeable ions of the membrane to convert the electrolyte of the eluent to weakly ionized form, followed by detection of the ions.

Another membrane suppressor device is disclosed in U.S. Pat. No. 4,751,004. There, a hollow fiber suppressor is packed with polymer beads to reduce band spreading. There is a suggestion that such packing may be used with other membrane forms. Furthermore, there is a suggestion that the function of the fiber suppressor is improved by using ion exchange packing beads. No theory is set forth as to why such particles would function in an improved manner.

Another suppression system is disclosed in U.S. Pat. No. 4,459,357. There, the effluent from a chromatographic column is passed through an open flow channel defined by flat membranes on both sides of the channel. On the opposite sides of both membranes are open channels through which regenerant solution is passed. As with the fiber suppressor, the flat membranes pass ions of the same charge as the exchangeable ions of the membrane. An electric field is passed between electrodes on opposite sides of the effluent channel to increase the mobility of the ion exchange. One problem with this electrodialytic membrane suppressor system is that very high voltages (50-500 volts DC) are required. As the liquid stream becomes deionized, electrical resistance increases, resulting in substantial heat production. Such heat is detrimental to effective detection because it greatly increases noise and decreases sensitivity.

In U.S. Pat. No. 4,403,039, another form of electrodialytic suppressor is disclosed in which the ion exchange membranes are in the form of concentric tubes. One of the electrodes is at the center of the innermost tube. One problem with this form of suppressor is limited exchange capacity. Although the electrical field enhances ion mobility, the device is still dependent on diffusion of ions in the bulk solution to the membrane.

Another form of suppressor is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site-to-site transfer paths across the effluent flow channel so that suppression capacity is no longer limited by diffusion of ions in the bulk solution to the membrane. A sandwich suppressor is also disclosed including a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant. The patent also discloses the possibility of using water to replace the regenerant solution in the electrodialytic mode.

In one form of sandwich suppressor of the foregoing type sold by Dionex Corporation for more than one year, for cation analysis, sulfonated and aminated screens of capacity similar to that of the eluent channel were disposed in the regenerant channel. The purpose of the sulfonated screen was to allow improved lifetime under solvent conditions.

U.S. Pat. No. 5,045,204 discloses an electrodialytic device using an ion exchange membrane separating two flowing solutions in flow-through channels for generating a high purity chromatography eluent (e.g., NaOH). Water is electrolyzed in a product channel to provide the source of hydroxide ion for sodium which diffuses across the membrane. The patent discloses a mode of eliminating hydrogen gas generated in the product channel.

U.S. Pat. No. 5,248,426 discloses a suppressor of the general type described in U.S. Pat. No. 4,999,098 in an ion chromatography system in which the effluent from the detector is recycled to the flow channel(s) in the suppressor adjacent the sample stream flow channel.

U.S. Pat. No. 5,597,481 disclosed a suppressor-type device of the foregoing type used in sample pretreatment to reduce or suppress matrix ions in the eluent of opposite charge to the analyte ions and then to analyze the analytes in their conductive forms. Using existing suppressor devices, ion exchange interactions and hydrophobic interaction of the analyte, particularly in the eluent flow channel, affects recovery of certain analytes such as oligonucleotides and oligosaccharides. In order to improve recovery, high concentrations of eluents coupled with solvents are generally used. Similarly, in order to elute certain highly charged multifunctional analytes from the chromatographic column, high concentrations of eluents are normally used. High concentrations of eluents, however, are not easily suppressed.

U.S. Pat. No. 6,077,434 discloses, methods and apparatus are provided of improved current efficiency. In one embodiment, an aqueous sample stream including analyte ions of one charge and matrix ions of opposite charge flows through a sample stream flow channel, while flowing an aqueous stream through an ion receiving flow channel separated therefrom by a first ion exchange membrane, and passing a current between the channels to reduce the concentration of the matrix ions. The sample stream flow channel has an upstream sample stream portion containing the matrix ions and an adjacent downstream portion in which the matrix ions have been suppressed. The upstream portion has an electrical resistance no greater than about 0.9 times that of the downstream portion. The ion receiving flow channel includes stationary flow-through first packing of ion exchange material. Neutral or low capacity packing may be disposed in the sample stream flow channel. In another embodiment, a second ion exchange membrane adjacent to the sample stream flow channel is used defining an ion source flow channel through which another aqueous stream flows. The first membrane has a net charge of no greater than about 0.9 times the net charge of the second membrane. In another embodiment, the downstream portion has a net charge of no greater than about 0.9 times the net charge of the upstream portion. In a further embodiment, current is passed at a first amperage between the upstream sample stream portion and an adjacent upstream ion receiving stream portion using first and second electrodes, and a second current is passed at a second lower amperage between the downstream sample stream portion and an adjacent downstream ion receiving stream portion using third and fourth electrodes.

There is a need to provide other ways to increase the capacity of suppressors and suppressor-like pretreatment devices to permit suppression of a high concentration of eluent. Similarly, in sample preparation applications it would be useful to have a suppressor with improved recovery of analytes and suppress high concentrations of eluent or mobile phase.

SUMMARY OF THE INVENTION

In one embodiment of the invention, a non-electrolytic apparatus is provided for treating an aqueous sample stream including analyte ions and matrix ions of opposite charge. The apparatus comprises a first ion exchange membrane capable of passing only ions of opposite charge to the analyte ions, a sample stream flow channel, a first aqueous stream ion receiving flow channel adjacent one side of the sample stream flow channel and separated therefrom by the first ion exchange membrane, and stationary flow-through first packing of ion exchange material disposed in the sample stream flow channel of the same charge as the first membrane and having a first ion exchange capacity for the matrix ions. The first ion receiving channel has an ion exchange capacity for the matrix ions less than about 25% of the first ion exchange capacity for the matrix ions. The application does not include electrodes disposed to apply an electric field between the sample stream flow channel and the first ion receiving flow channel.

In another embodiment, a chromatography apparatus including apparatus is provided for treating an aqueous sample stream including analyte ions and matrix ions of opposite charge, the apparatus comprising a chromatography separator having an inlet and an outlet, the inlet being in fluid communication with the sample stream. The treating apparatus is disposed upstream or downstream from the chromatography separator and comprises a first ion exchange membrane capable of passing only ions of opposite charge to the analyte ions, a sample stream flow channel, a first aqueous stream ion receiving flow channel adjacent one side of the sample stream flow channel and separated therefrom by the first ion exchange membrane. Stationary flow-through first packing of ion exchange material is disposed in the sample stream flow channel of the same charge as the first membrane and having a first ion exchange capacity for the matrix ions. The first ion receiving channel has an ion exchange capacity for the matrix ions less than about 25% of the first ion exchange capacity for the matrix ions.

In another embodiment, a non-electrolytic method is provided for treating an aqueous sample stream including analyte ions of one charge and matrix ions of opposite charge to the analyte ions. The method comprises flowing the sample stream through a sample stream flow channel, simultaneously flowing an aqueous stream through an ion receiving flow channel separated therefrom by a first ion exchange membrane capable of passing only ions of opposite charge to the analyte ions and of blocking bulk liquid flow to reduce the concentration of the matrix ions in an effluent from the sample stream flow channel, the sample stream flow channel having stationary flow-through first packing of ion exchange material disposed in the sample stream flow channel of the same charge as the first membrane and having a first ion exchange capacity for the matrix ions. The ion receiving channel has an ion exchange capacity for the matrix ions less than about 25% of the first ion exchange capacity for the matrix ion. No electric field is applied between the sample stream flow channel and the first ion receiving flow channel.

In another embodiment, a chromatography method is provided comprising flowing an aqueous sample stream including analyte ions of one charge and matrix ions of opposite charge to the analyte ions through a chromatography separator to separate the analyte ions. The sample stream including the separated analyte ions flows through a sample stream flow channel, and simultaneously flowing an aqueous stream through an ion receiving flow channel separated therefrom by a first ion exchange membrane capable of passing only ions of opposite charge to the analyte ions and of blocking bulk liquid flow to reduce the concentration of the matrix ions in an effluent from the sample stream flow channel, the sample stream flow channel having stationary flow-through first packing of ion exchange material disposed in the sample stream flow channel of the same charge as the first membrane and having a first ion exchange capacity for the matrix ions, the ion receiving channel having an ion exchange capacity for the matrix ions less than about 25% of the first ion exchange capacity for the matrix ion.

DETAILED DESCRIPTION OF THE PREFERRED EMBODIMENTS

Figure 1:
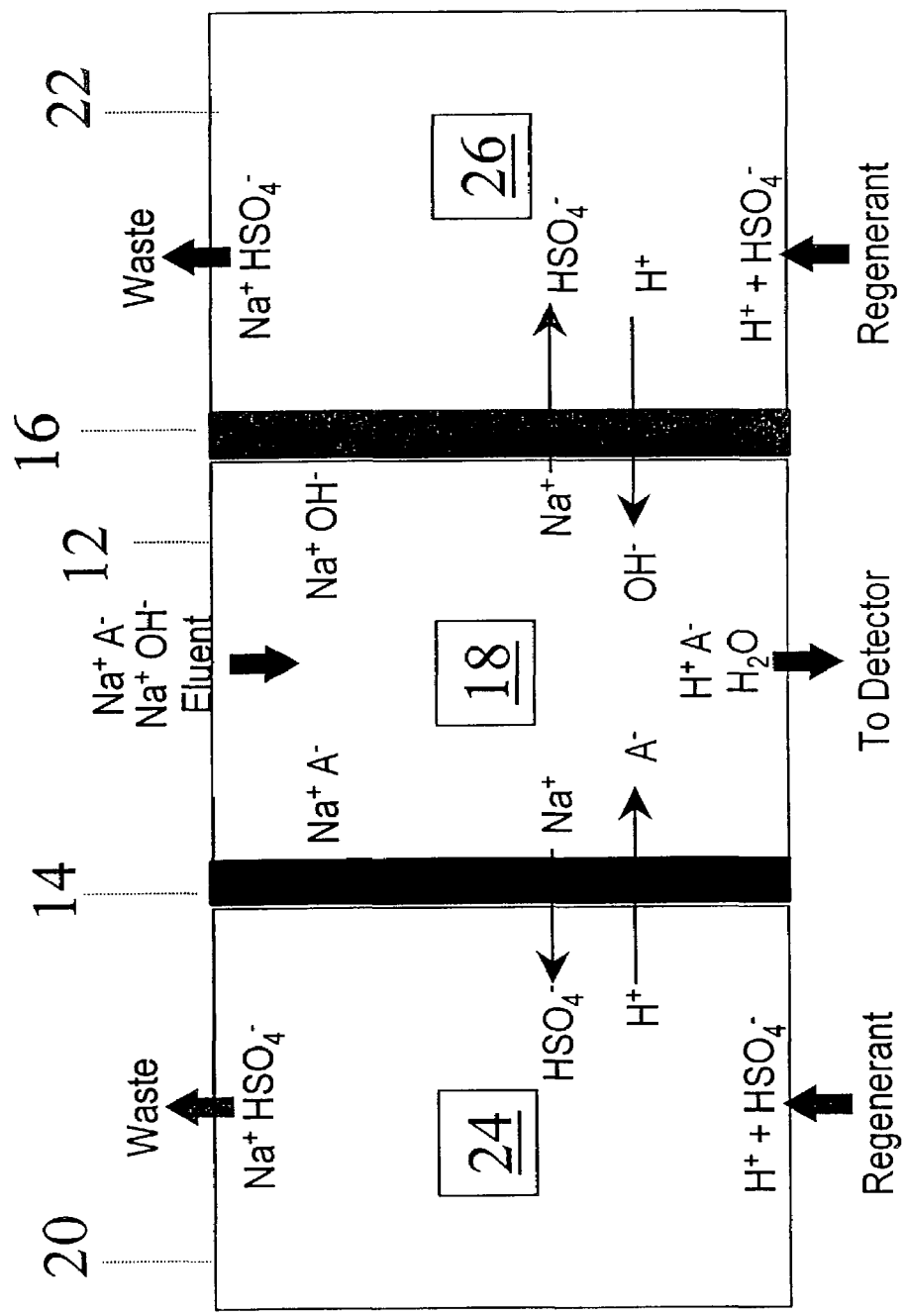
FIG. 1 is a schematic view of a suppressor according to the invention.

The system of the present invention is useful for determining a large number of ionic analyte so long as the ions are solely anions or solely cations. Suitable samples include surface waters and other liquids such as industrial chemical waste, body fluids, beverages such as fruits, wines and drinking water.

The present invention is directed to a method and apparatus for treating an aqueous sample stream including analyte ions of one charge and matrix ions of opposite charge. In one application, the treatment is in a suppressor for ion chromatography and the matrix ions are the electrolyte ions in the eluent of opposite charge to the analyte ions. In another application, the method and apparatus is used for pretreating an aqueous sample stream prior to analysis, preferably including separation on a chromatography column. In this instance, the matrix ions typically are compounds of high ionic strength in the sample stream (e.g., commercial sodium hydroxide) which can obscure the sample peaks by large interfering peaks of the sample matrix ions. Such matrix ions can severely change chromatography because the sample matrix ion is of such high concentration it becomes the major eluting ion, temporarily overriding the eluent. A typical minimum concentration to warrant pretreatment is when the matrix ion is at least ten times the molar ionic concentration of the chromatographic eluent. Such a system to which the present improvement in suppression capacity is applicable to devices set forth in Stillian, et al., U.S. Pat. No. 5,597,481, incorporated herein by reference.

As used herein, the term "matrix ion" refers to either the electrolyte in an eluent used for chromatography which is suppressed or whose concentration is reduced to non-interfering levels after separation and prior to detection, or to matrix ions in a sample stream whose concentration is significantly reduced prior to separation and/or detection. Since, in either case, the matrix ions are suppressed in the device, the term "suppressor" will be used generically to include a suppressor for ion chromatography and a pre-treatment device including the modifications of the present invention.

For the analysis of anions, the matrix ions typically are a base (e.g., sodium hydroxide or other alkyl metal hydroxides). Other matrix compounds include sodium carbonate, sodium bicarbonate, ammonium hydroxide, or alkyl ammonium hydroxide. For cation analysis, the matrix ions typically are an acid such as a common mineral or organic acid (e.g., sulfuric acid, phosphoric acid or methane sulfonic acid).

The term "packing" refers to stationary flow-through solid material disposed in a flow channel of the suppressor. It can be a screen or a porous monolithic matrix, a resin particle bed or other form. It can be strongly charged, weakly charged or of neutral charge, as will be explained. The term packing is alternatively called "bridging means."

During suppression, the conductivity and noise caused by matrix ions in an analysis stream is reduced. The present invention serves to increase the capacity of the suppressors described above. Various embodiments of such suppressors will be described herein.

The specific purpose of the suppressor stage in ion chromatography is to reduce the conductivity and noise of the analysis stream background while enhancing the conductivity of the analytes (i.e., increasing the signal/noise ratio), while maintaining chromatographic efficiency. Thus, the following parameters bear upon the performance of the suppressor: (1) dynamic capacity of suppression, measured as $\mu Eq./min$ of eluent for each device; and (2) background conductivity measured as $\mu S/cm$ per device.

In one embodiment, a suppressor of increased capacity according to the invention can be used in a chromatography system using a chemical or electrochemical suppressor of the type described in Pohl, et al., U.S. Pat. No. 4,999,098, incorporated herein by reference. A chemical suppressor (i.e., one which relies on chemical regenerant solution and in which an electric current is not applied and so which does not require electrodes) is preferred herein. In some instances, the invention may be applicable to electrochemical suppressors. The invention will be described with respect to an ion chromatography system in which a chemical suppressor is disposed between the chromatography column and detector.

FIG. 1 illustrates a chemical suppressor for performing the present invention. As illustrated in FIG. 1 of the '098 patent, the suppressor can be used in a system which includes a chromatographic separator, typically in the form of a chromatographic column, which is packed with a chromatographic separation medium. In one embodiment referred to above, such medium is in the form of ion-exchange resin. In another embodiment, the separation medium is a porous hydrophobic chromatographic resin with essentially no permanently attached ion-exchange sites. This other system is used for mobile phase ion chromatography (MPIC) as described in U.S. Pat. No. 4,265,634. An ion exchange site-forming compound, including hydrophobic portion and an ion-exchange site, is passed through the column and is reversibly adsorbed to the resin to create ion-exchange sites.

Arranged in series with the chromatographic column is the suppressor serving to suppress the conductivity of the electrolyte of the eluent from the column but not the conductivity of the separated ions. The conductivity of the separated ions is usually enhanced in the suppression process.

As further illustrated in FIG. 1 of the '098 patent, the effluent from the suppressor is directed to a detector, preferably in the form of flow-through conductivity cell, for detecting all the resolved ionic species therefrom. A suitable sample is supplied through a sample injection valve and passed through the apparatus in the solution of eluent from an eluent source or reservoir drawn by a pump, and then through the sample injection valve. The chromatography effluent solution leaving the column is directed to the suppressor wherein the electrolyte is converted to a weakly conducting form. The chromatography effluent with separated ionic species is then treated by the suppressor and passed through the conductivity cell. In the conductivity cell, the presence of ionic species produces an electrical signal proportional to the amount of ionic material. Such signal is typically directed from the cell 12 to a conductivity meter, not shown, thus permitting detection of the concentration of separated ionic species.

Referring to FIG. 1 herein, a device is schematically illustrated in the form of a sandwich membrane suppressor device including a central sample stream flow channel defined on both sides by ion-exchange membranes to the exterior of which are ion receiving flow channels. The specific structure of a chemical sandwich suppressor may be of the type illustrated in FIGS. 2 and 3 of the '098 patent but, preferably without the electrodes. In one embodiment, the device includes means defining a sample stream flow channel in the form of a sample stream compartment, partially bounded by a sample stream gasket defining a central cavity. To minimize dead space in the cavity, it is preferable to form both ends of the flow channels in a peak or V-shape. Stationary flow-through packing, preferably bridging means in the form of a sample stream screen, may be disposed in the cavity. Ion exchange membrane sheets are mounted to extend along opposite sides of the sample stream screen and, together with a gasket, define the outer perimeter of the sample stream flow channel. External support blocks may be provided in the form of a rigid nonconductive material, such as polymethylmethacrylate, or polyether-ether ketone (PEEK) and serve to provide structural support for the remainder of membrane the device.

The ion-exchange membrane sheets may be of a type such as disclosed in the '098 patent. In particular, such sheets may be cation-exchange or anion-exchange membranes with polyethylene, polypropylene, polyethylene-vinylacetate-based substrates. Other suitable substrates include poly-vinylchloride or polyfluorocarbon-based materials. The substrate polymer is solvent and acid or base resistant. Such substrates are first grafted with suitable monomer for later functionalizing. Applicable monomers include styrene and alkylstyrenes such as 4-methylstyrene, vinylbenzylchloride or vinylsulfonates, vinylpyridine and alkylvinylpyridines. As an example, to form a cation-exchange membrane, the sheets grafted with styrene monomers are functionalized suitably with chlorosulfonic acid, sulfuric acid, or other $SO_2$ or $SO_3$ sources. To form an anion-exchange membrane, the sheets grafted with vinylbenzylchloride monomers are functionalized with alkyl tertiary amines such as trimethylamine or tertiary alkanolamines, such as dimethylethanolamine. Particularly effective membranes are no more than 10 mil thick, and preferably no more than 2-5 mil when dry. Suitable polyethylene substrate membranes of the foregoing type are provided by RAI Research Corp., Hauppauge, N.Y. (the cation exchange membrane provided under designation R5010 (0.008 inch thick) and the anion-exchange membrane under designation R4015 (0.004 inch thick)). Other cation exchange membranes supplied by the same company which are fluorocarbon based include R1010 (0.002 inch thick) and R4010 (0.004 inch thick).

For a flat sheet suppressor, one embodiment of the packing includes continuous portions which extend substantially the entire distance of the flow channels in which they are used and transverse to flow. In an alternate embodiment illustrated in FIG. 6 of the '098 patent, only one membrane is used which separates an ion receiving flow channel from sample stream flow channel 31. The packing, when used, preferably defines a continuous convoluted flow-through passageway in the flow channel in which it is disposed along substantially the entire length of the membrane. This creates turbulence and thus increases the efficiency of mixing and transfer of the ions across the membrane as described below. The physical configuration of the packing is preferably a screen.

FIG. 1 herein is a schematic view of a suppressor used in the chemical mode. The overall structure of the device can be the same as a commercial AMMS® or CMMS® suppressor sold by Dionex Corporation with the exception of the ion exchange capacity of the packing in the regenerant flow channels. FIG. 1 will first be described with respect to a commercial anion membrane suppressor, such as one sold by Dionex Corporation under the trademark AMMS®. In general terms, the device can be used for treating an aqueous stream including analyte ions and matrix ions of opposite charge. For the analysis of anions illustrated in FIG. 1 as $A^-$ in a $Na^+A^-$ salt, the device 10 includes an eluent flow channel 12 bounded on both sides along the flow path by cation exchange membranes 14 and 16 capable of passing only ions of opposite charge to the analyte ions, e.g., capable of passing the sodium ions, assuming a sodium hydroxide eluent. Eluent flow channel 12, also termed a sample flow channel, includes stationary flow-through first packing 18 of ion exchange material having the same charge as membranes 14 and 16, i.e., a positive charge for the analysis of anions. The function of that flow-through packing is as described above. Regenerant or ion receiving flow channels 20 and 22, respectively, are disposed on the opposite side of membranes 14 and 16, respectively, from flow channel 12. The low ion exchange capacity or absence of capacity in flow channels 20 and 22 provide for increased current capacity for the suppressors of the present invention as will be described below. Packing 24 and 26, in the embodiments in which packing are present, is disposed in flow channels 20 and 22, respectively.

As set forth above, the system of the present invention is applicable to the use of the apparatus for pretreating an aqueous stream prior to separation by chromatography or for use as a suppressor in ion exchange chromatography downstream from the chromatography column. Thus, the present description will be referred to in general terms with the eluent flow channel 12 of device 10 being referred to interchangeably as an eluent flow channel or a sample flow channel and the regenerant flow channels 20 and 22 will also be referred to as ion receiving flow channels. This is because, whether the device 10 is used as a pretreatment device or a suppressor, the matrix ion of opposite charge to the analyte ion flow into the ion receiving flow channels 20 and 22.

Referring again to FIG. 1, the flow pattern and configuration for the Dionex AMMS® device and that of the present invention are the same. Thus, in one form, the device has a high capacity cation exchange packing 18, such as cation screens, in the eluent flow channel, such as described in U.S. Pat. No. 4,998,098. In operation as a suppressor, the cations from the eluent in the sample are driven across membranes 14 and 16 and exchanged for hydronium ions supplied from an external chemical reservoir. FIG. 1 illustrates device 10 as a suppressor. There, NaOH is used as an eluent and so the analyte ions $A^-$ in the sample stream flow channel are in the sodium ion salt form ($Na^+A^-$). The illustrated chemical regenerant is a strong acid, as sulfuric acid, flowing in the ion receiving channels 22 and 24 countercurrently to the eluent stream. The sodium ions flow into an ion receiving channel to form a salt, e.g., of $NaHSO_4$. The analyte ions $A^-$ exit the device 10 in acid form $H^+A^-$ and flow to a detector, not shown, typically an ion conductivity detector. Except for the ion exchange capacity of the packing in the ion receiving channels, such a chemical regenerant system is described in the prior art such as in U.S. Pat. No. 4,999,098.

As set forth above, device 10 can be used for treating an aqueous stream including analytes of one charge and matrix ions of opposite charge to the analyte ions. The samples stream flows through the sample stream flow channel while an aqueous stream flows through at least one ion receiving flow channel separated therefrom by the ion exchange membrane capable of passing of ions of opposite charge to the analyte ions and the blocking of bulk liquid flow. As illustrated, the device is in a flat sandwich form. However, the invention is also applicable to a device using a single membrane in a single ion receiving channel or in a tubular form. Also, the device is illustrated using countercurrent flow between he sample stream flow channel and ion receiving flow channel. Alternatively, flow can be concurrent.

Device 10 of the present invention has a substantially lower ion exchange capacity for the matrix ion in the ion receiving channels 20 and 22 than in the sample stream flow channel 12. Thus, according to the invention, the ion exchange capacity for the matrix ions in the ion receiving channel(s) is less than about 25% of that in the sample stream flow channel, preferably less than 20%, 15%, 10%, 5% or less, and may have essentially no capacity. The term "ion exchange capacity" in the ion receiving flow channel(s) refers to the capacity of packing for the removed ions, if present in such channel(s). Thus, in one embodiment, there is no ion exchange capacity for the matrix ions in the ion receiving flow channel(s). This could be accomplished by having no packing in the ion receiving channel(s) or by the use of a neutral screen or a neutral packed particle bead or by use of an ion exchange screen or resin with opposite functionality only to the removed ions in the ion receiving flow channel(s). There, the ion receiving flow channel(s) are substantially free of ion exchange capacity for the matrix ions.

The ion exchange capacity for the matrix ions in the sample stream flow channel is typically as used for the eluent flow channel of a membrane suppressor of the type sold by Dionex Corporation under the AMMS® mark and as described in U.S. Pat. No. 4,999,098. Suitable ranges of ion exchange capacity in the sample stream flow channel are from 0.01 to 5 meqv/gm, preferably 0.05 to 1 meqv/gm, and more preferably from 0.1 to 0.3 meqv/gm. The ion exchange capacity in the sample stream flow channel is beneficial particularly when the regenerant is consumed. It permits the device to have significant static capacity so that the process of suppression can continue uninterrupted for some time.

In the above embodiment using packing of very low capacity or no capacity for the matrix ions (cations for anion analysis) in the ion receiving flow channel(s), the removed cations, e.g., $Na^+$, are substantially unretained by the regenerant screen in such flow channels. An advantage of this lack of retention capacity is that the removed cations are quickly equilibrated, the cations are quickly removed from the suppressor devices and suppression capacity is improved. Also, the cost of the device is reduced because the neutral function screens are cheaper to manufacture. Further, unfunctionalized neutral materials are less likely to swell in the presence of a solvent and are more compatible with solvents. This reduces back pressure in the presence of a solvent, thus reducing the amount of pressure required to dispense the regenerant solution into the regenerant flow channels.

As an alternative to the neutral screens, packing lightly functionalized for low ion exchange capacity for the matrix ions may be used, preferably less than the aforementioned percentages of the capacity of the ion exchange packing in the sample stream flow channel.

In another embodiment, the matrix ion receiving channel includes packing of opposite charge to the matrix ion. Thus, for anion analysis wherein the eluent is NaOH, an aminated regenerant screen can be used in the matrix ion receiving channel. The capacity of such packing is preferably relatively low for the removed cations, e.g., from 0.01 to 0.1 meqv/gm, preferably from 0.0 to 0.02 meqv/gm. This results in no substantial retention of the removed cation and can result in increased suppressor capacity because the ions are removed faster from the regenerant channel and the suppressor device.

Although the above system has been described with respect to anion analysis, it is also applicable to cation analysis with a reversal of polarities of the membranes and reagents.

The above system illustrates an ion exchange screen as the preferred flow-through ion exchange packing. However, it should be understood that other ion exchange packing may also be employed for the sandwich suppressor or other relatively flat suppressor. For example, ion exchange or neutral particles may be packed in the regenerant flow channels for this purpose. Here, it would be preferable to include some mode to keep the ion exchange particles in the device by using a porous polymeric support that has smaller pores than the resin being used, such as sintered polyethylene available from General Polymeric.

A tubular form of suppressor of the present invention may also be used as illustrated in U.S. Pat. No. 4,999,098, but preferably in the chemical mode.

In order to illustrate the present invention, the following examples of its practice in the chemical mode are provided.

EXAMPLE 1

The performance in terms of dynamic capacity of a standard AMMS III suppressor from Dionex Corporation was compared to a device of the present invention. The device of the present invention was assembled by fitting neutral regenerant screens in place of the functionalized cation exchange regenerant screens and using standard AMMS III suppressor components. A Dionex DX500 ion chromatography system was used for this testing. The dynamic suppression capacity was determined by pumping at 1 ml/min various concentrations of NaOH by conventional proportioning. The regenerant was 100 mN sulfuric acid pumped at 10 ml/min (conventional chemical suppression mode).

Results: The dynamic capacity of the standard AMMS III suppressor was measured as 170 ueqv/min. The device of the present invention showed a dynamic capacity of 210 ueqv/min which was an increase of 23% in capacity. Thus, removing the retention of the eluent cation in the regenerant chamber as per the current invention resulted in improved operational capacity.

EXAMPLE 2

The experimental setup was similar to Example 1 except the regenerant was 150 mN sulfuric acid and was dispensed using the displacement chemical regeneration approach of U.S. Pat. No. 6,436,719.

Results: The dynamic capacity under these conditions for a standard suppressor was 70 ueqv/min. The device of the present invention on the other hand showed a capacity of 90 ueqv/min. A 29% increase in capacity was observed as per the present invention.

EXAMPLE 3

The performance in terms of dynamic capacity of a standard CMMS III suppressor from Dionex Corporation was compared to a device of the present invention. The device of the present invention was assembled by fitting neutral regenerant screens in place of the functionalized regenerant screens using standard CMMS III suppressor components. A DX500 ion chromatography system was used for this testing. The dynamic suppression capacity was determined by pumping at 1 ml/min various concentrations of MSA by conventional proportioning. The regenerant was 100 mN tetrabutylammonium hydroxide base pumped at 10 ml/min (conventional chemical suppression mode). The dynamic capacity of the standard CMMS III suppressor was measured as 65 ueqv/min.

Results: The device of the present invention showed a dynamic capacity of 100 ueqv/min which was an increase of 53% in capacity. Thus, removing the retention of the anion in the regenerant chamber as per the present invention resulted in improved operational capacity.

EXAMPLE 4

The experimental setup was similar to Example 3 except the regenerant was dispensed using the displacement chemical regeneration approach of U.S. Pat. No. 6,436,719.

Results: The dynamic capacity under these conditions for a standard suppressor was 35 ueqv/min. The device of the present invention on the other hand showed a capacity of 55 ueqv/min. A 57% increase in capacity was observed as per the present invention.

EXAMPLE 5

An AMMS III suppressor was assembled with cation exchange based lightly functionalized regenerant screens with a cation exchange capacity of 0.01 meqv/gm by replacing the standard regenerant screens that had a capacity of 0.3 meqv/gm. This device when tested for dynamic capacity under conditions outlined in Example 1 showed performance similar to the device of Example 1.

EXAMPLE 6

An AMMS III suppressor was assembled with anion exchange based aminated regenerant screen in place of the standard cation exchange based sulfonated screen in the two regenerant chambers. The suppressor was tested following the conditions outlined in Example 1. This unit also showed performance comparable to the suppressor of Example 1.

What is claimed is:

1. A non-electrolytic method for treating an aqueous sample stream including analyte ions of one charge and matrix ions of opposite charge to said analyte ions, said method comprising flowing the sample stream through a sample stream flow channel, simultaneously flowing an aqueous stream through an ion receiving flow channel separated therefrom by a first ion exchange membrane capable of passing only ions of opposite charge to said analyte ions and of blocking bulk liquid flow to reduce the concentration of said matrix ions in an effluent from said sample stream flow channel, said sample stream flow channel having stationary flow-through first packing of ion exchange material disposed in the sample stream flow channel of the same charge as said first membrane and having a first ion exchange capacity for said matrix ions, said ion receiving channel having a second flow-through exchange packing of opposite charge to said first ion exchange packing disposed therein, an electric field not being applied between said sample stream flow channel and said first ion receiving flow channel.

2. The method of claim 1 in which said first ion receiving flow channel is substantially free of ion exchange capacity for said matrix ions.

3. The method of claim 1 further comprising flowing said aqueous sample stream through a chromatographic separator to separate the analyte ions prior to flowing said sample stream through said sample stream flow channel, and then detecting said separated analyte ions.

* * * * *